United States Patent [19]

Takahashi

[11] Patent Number: 4,693,568
[45] Date of Patent: Sep. 15, 1987

[54] IMAGE TRANSMISSION OPTICAL SYSTEM FOR AN ENDOSCOPE

[75] Inventor: Susumu Takahashi, Tokyo, Japan

[73] Assignee: Olympus Optical Co., Ltd., Tokyo, Japan

[21] Appl. No.: 777,679

[22] Filed: Sep. 19, 1985

[30] Foreign Application Priority Data

Sep. 25, 1984 [JP] Japan .................. 59-200140

[51] Int. Cl.⁴ .................. G02B 9/34; G02B 23/00
[52] U.S. Cl. .................. 350/469; 350/573
[58] Field of Search .............. 350/476, 471, 469, 573

[56] References Cited

U.S. PATENT DOCUMENTS 4,168,882 9/1979 Hopkins .................. 350/471

FOREIGN PATENT DOCUMENTS 0537460 3/1922 France .................. 350/471
49-5993 2/1974 Japan .
52-4245 1/1977 Japan .

Primary Examiner—John K. Corbin
Assistant Examiner—Rebecca D. Gass
Attorney, Agent, or Firm—Cushman, Darby & Cushman

[57] ABSTRACT

An image transmission optical system for an inflexible-type endoscope comprising two rod-like biconvex lenses, and two thick meniscus lenses which are arranged between the two rod-like biconvex lenses so that convex surfaces of the two thick meniscus lenses face each other, the image transmission optical system being arranged that the brightness is uniform, and curvature of field and astigmatic difference are corrected favorably.

11 Claims, 15 Drawing Figures

IMAGE TRANSMISSION OPTICAL SYSTEM FOR AN ENDOSCOPE

BACKGROUND OF THE INVENTION (a) Field of the Invention

The present invention relates to an image transmission optical system for an endoscope and, more particularly, to an image transmission optical system to be used with an inflexible-type endoscope or the like which is arranged to transmit an image by using a plural number of relay lenses.

(b) Description of the Prior Art

An inflexible-type endoscope arranged to transmit an image by using a plural number of relay lenses is composed that an objective 2, image transmission optical systems 3, 3', ... and eyepiece 4 are arranged in an outer tube 1 in the order from the object side as shown in FIG. 13. The above-mentioned type of endoscope is arranged that an image Q of an object formed by the objective 2 is relayed in turn as $Q_1$, $Q_2$, ... by means of respective image transmission optical systems 3, 3', ... , and the last image $Q_L$ is observed through the eyepiece 4. The image transmission optical system disclosed in Japanese published examined patent application No. 5993/74 is known as an image transmission optical system to be used with the above-mentioned type of endoscope. Said known image transmission optical system is arranged that two rod-like cemented doublets, each consisting of a positive lens element and negative lens element cemented together, are arranged so that the negative lens elements thereof face each other as shown in FIG. 14.

In case of said known image transmission optical system, spherical aberration, coma and chromatic aberration are corrected favourably. However, curvature of field is not corrected satisfactorily and, moreover, astigmatic difference is caused. Therefore, when the number of image transmission optical systems constituting the endoscope becomes large, curvature of field and astigmatic difference are accumulated and become very large. As a result, it is impossible to bring both of the central portion and marginal portion of the image into focus at the same time.

The image transmission optical system disclosed in Japanese published unexamined patent application No. 4245/77 is known as an image transmission optical system arranged to eliminate the above-mentioned disadvantage. Said known image transmission optical system is composed that two rod-like meniscus lenses 7 and 8, which are arranged so that the concave surfaces thereof face each other, are arranged between two rod-like biconvex lenses 5 and 6 as shown in FIG. 15 and is arranged that curvature of field and astigmatic difference are corrected by means of negative action of an air lens 9 which is formed by those two concave surfaces.

However, when an image is transmitted by using said known image transmission optical system, heights of rays that pass the optical system become the highest at the surfaces 10 and 11 on the inner sides of the biconvex lenses 5 and 6. As a result, as it is evident from FIG. 15, upper rays of offaxial rays are eclipsed at a position (position shown by the arrow mark A in FIG. 15) of long distance from the object point and, consequently, the upper NA becomes small. On the other hand, paraxial rays are eclipsed at the position shown by the arrow mark B. As described in the above, in case of said known image transmission optical system, paraxial rays and offaxial rays are eclipsed at positions which are largely different from each other. Consequently, NA of paraxial rays and NA of offaxial rays become largely different from each other, and the brightness at the central portion of field becomes considerably different from the brightness at the marginal portion of field. The above-mentioned disadvantage becomes very conspicuous especially when the length of the meniscus lenses 7 and 8 is increased in order to prevent the lenses from inclining in the outer tube.

SUMMARY OF THE INVENTION

It is, therefore, a primary object of the present invention to provide an image transmission optical system for an endoscope of which the difference between the brightness at the central portion of field and brightness at the marginal portion is small and, at the same time, curvature of field and astigmatic difference are also corrected favourably.

The image transmission optical system according to the present invention comprises, as shown in FIG. 1, two biconvex lenses 12 and 13, which are arranged at a certain distance from each other, and two thick meniscus lenses 18 and 19 which are arranged between said biconvex lenses 12 and 13 so that the convex surfaces 14 and 15 of said thick meniscus lenses 18 and 19 face each other. The optical system arranged as described in the above makes it possible to favourably correct curvature of field and astigmatic difference by means of negative actions of the concave surfaces 16 and 17 of said thick meniscus lenses 18 and 19. Besides, as the thick meniscus lenses 18 and 19 are arranged so that the convex surfaces thereof face each other, the distance between the position where paraxial rays are eclipsed and position where offaxial rays are eclipsed becomes short. That is, upper rays of offaxial rays are limited by the surface 15, i.e., at the position shown by the arrow mark A in FIG. 1, and paraxial rays and lower rays of offaxial rays are limited by the surface 14, i.e., at the position shown by the arrow mark B. Therefore, the difference between NA at the central portion of field and NA at the marginal portion of field becomes small and, consequently, the brightness becomes uniform.

To correct curvature of field, it is preferable to arrange that the concave surfaces 16 and 17 of the meniscus lenses 18 and 19 have strong negative power. On the other hand, said surfaces also contribute to correction of spherical aberration and coma. Therefore, to correct all of said aberrations in well balanced state, it is preferable to decide refractive powers of respective surfaces so as to fulfill the following condition:

$$1 > f(\phi_1 + \phi_2 + \phi_3) > -1 \tag{1}$$

where, reference symbol f represents the total focal length of a system composed of three surfaces, i.e., the surface 25 on the exit side of the biconvex lens 12 (or the surface 26 on the entrance side of the biconvex lens 13) and surfaces on both sides of the thick meniscus lens 18 (or the thick meniscus lens 19), reference symbol $\phi_1$ represents refractive power of the surface 25 on the exit side of the biconvex lens 12 (or the surface 26 on the entrance side of the biconvex lens 13), reference symbol $\phi_2$ represents refracitve power of the surface 16 on the entrance side of the meniscus lens 18 (or the surface 17 on the exit side of the meniscus lens 19), and reference symbol $\phi_3$ represents refractive power of the surface 14 on the exit side of the meniscus lens 18 (or the surface 15 on the entrance side of the menisucs lens 19).

If the value defined by the condition shown in the above becomes larger than the upper limit thereof, the negative action of the surface 16 (or the surface 17) becomes weak, and curvature of field cannot be corrected satisfactorily. On the other hand, if the value defined by said condition becomes smaller than the lower limit thereof, said negative action becomes strong, and curves of spherical aberration and coma tend to become large.

DETAILED DESCRIPTION OF THE PREFERRED EMBODIMENTS

Now, preferred embodiments of the image transmission optical system for an endoscope according to the present invention are shown below.

Figure 1:
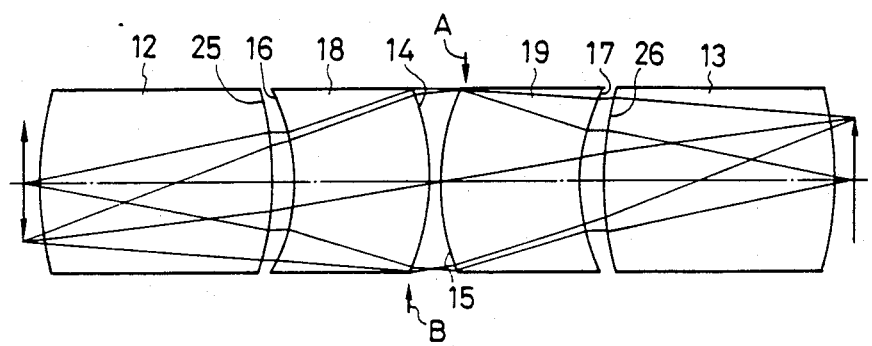
FIG. 1 shows a sectional view illustrating the composition of the image transmission optical system for an endoscope according to the present invention.
Figure 2:
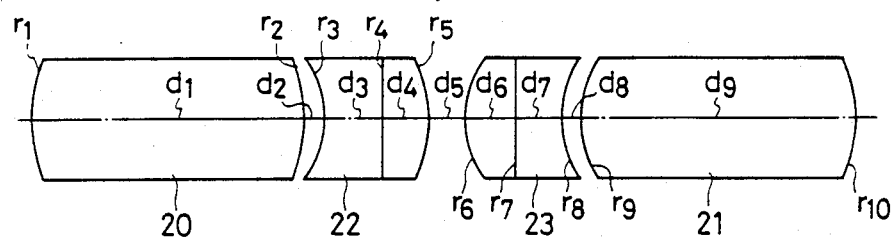
FIG. 2 shows a sectional view of Embodiment 1, 2, 3 and 4 of the present invention.

Embodiment 1 of the image transmission optical system according to the present invention comprises, as shown in FIG. 2, rod-like biconvex lenses 20 and 21, and thick meniscus lenses 22 and 23 which are arranged between said biconvex lenses 20 and 21 so that the convex surfaces of said thick meniscus lenses 22 and 23 face each other, and is arranged to be symmetrical in respect to the center of the airspace between said meniscus lenses 22 and 23. Besides, Embodiment 1 have the numerical data shown below.

$r_1 = 17.792$
$d_1 = 38.89$ $\quad n_1 = 1.62$ $\quad \nu_1 = 36.25$
$r_2 = -16.305$
$d_2 = 0.62$
$r_3 = -7.583$
$d_3 = 4.49$ $\quad n_2 = 1.62$ $\quad \nu_2 = 36.25$
$r_4 = \infty$
$d_4 = 2.34$ $\quad n_3 = 1.6968$ $\quad \nu_3 = 55.52$
$r_5 = -11.618$
$d_5 = 1.00$
$r_6 = 11.618$
$d_6 = 2.34$ $\quad n_4 = 1.6968$ $\quad \nu_4 = 55.52$
$r_7 = \infty$
$d_7 = 4.49$ $\quad n_5 = 1.62$ $\quad \nu_5 = 36.25$
$r_8 = 7.583$
$d_8 = 0.62$
$r_9 = 16.305$
$d_9 = 38.89$ $\quad n_6 = 1.62$ $\quad \nu_6 = 36.25$
$r_{10} = -17.792$
$f = 36.82, \phi_1 = 0.06, \phi_2 = -0.082, \phi_3 = 0.038$
$f(\phi_1 + \phi_2 + \phi_3) = 0.59$ In the numerical data shown in the above, reference symbols $r_1$ through $r_{10}$ respectively represent radii of curvature of respective lens surfaces, reference symbols $d_1$ through $d_9$ respectively represent distances between respective lens surfaces, reference symbols $n_1$ through $n_6$ respectively represent refractive indices of respective lenses, reference symbols $\nu_1$ through $\nu_6$ respectively represent Abbe's numbers of respective lenses, reference symbol f represents the total focal length of a system from the surface $r_2$ to the surface $r_5$, and reference symbols $\phi_1$, $\phi_2$ and $\phi_3$ respectively represent refractive powers of the surfaces $r_2$, $r_3$ and $r_4$.

Embodiment 2 of the present invention has the lens configuration shown in FIG. 2 in the same way as Embodiment 1 and has the numerical data shown below.

$r_1 = 15.596$
$d_1 = 38.89$ $\quad n_1 = 1.51633$ $\quad \nu_1 = 64.15$
$r_2 = -14.9578$
$d_2 = 0.62$
$r_3 = -7.241$
$d_3 = 4.49$ $\quad n_2 = 1.62$ $\quad \nu_2 = 36.25$
$r_4 = \infty$
$d_4 = 2.34$ $\quad n_3 = 1.734$ $\quad \nu_3 = 51.49$
$r_5 = -11.637$
$d_5 = 0.81$
$r_6 = 11.637$
$d_6 = 2.34$ $\quad n_4 = 1.734$ $\quad \nu_4 = 51.49$
$r_7 = \infty$
$d_7 = 4.49$ $\quad n_5 = 1.62$ $\quad \nu_5 = 36.25$
$r_8 = 7.241$
$d_8 = 0.62$
$r_9 = 14.9578$
$d_9 = 38.89$ $\quad n_6 = 1.51633$ $\quad \nu_6 = 64.15$
$r_{10} = -15.596$
$f = 39.625, \phi_1 = 0.063, \phi_2 = -0.086, \phi_3 = 0.035$
$f(\phi_1 + \phi_2 + \phi_3) = 0.48$ Embodiment 3 of the present invention has the lens configuration shown in FIG. 2 and has numerical data shown below.

$r_1 = 17.544$
$d_1 = 33.36$ $\quad n_1 = 1.51633$ $\quad \nu_1 = 64.15$
$r_2 = -9.122$
$d_2 = 3.03$
$r_3 = -5.48$
$d_3 = 5.69$ $\quad n_2 = 1.56732$ $\quad \nu_2 = 42.83$
$r_4 = \infty$
$d_4 = 3.37$ $\quad n_3 = 1.51633$ $\quad \nu_3 = 64.15$
$r_5 = -9.121$
$d_5 = 2.27$
$r_6 = 9.121$
$d_6 = 3.37$ $\quad n_4 = 1.51633$ $\quad \nu_4 = 64.15$
$r_7 = \infty$
$d_7 = 5.69$ $\quad n_5 = 1.56732$ $\quad \nu_5 = 42.83$
$r_8 = 5.48$
$d_8 = 3.03$
$r_9 = 9.122$
$d_9 = 33.36$ $\quad n_6 = 1.51633$ $\quad \nu_6 = 64.15$
$r_{10} = -17.544$
$f = 36.498, \phi_1 = 0.057, \phi_2 = -0.103, \phi_3 = 0.057$
$f(\phi_1 + \phi_2 + \phi_3) = 0.40$ Embodiment 3 is arranged that refractive indices of all lenses are smaller than 1.6 (n<1.6) and Abbe's numbers of all lenses are larger than 40 ($\nu$>40). Glass materials of which refractive indices and Abbe's numbers are in the above-mentioned ranges have such characteristics that the spectral transmittance is flat in the visible region and, therefore they show excellent colour rendering especially when they are used for a system comprising a large number of image transmission optical systems.

Embodiment 4 of the present invention has the lens configuration shown in FIG. 2 and numerical data shown below.

| | | |
|---|---|---|
| $r_1 = 17.698$ | | |
| $d_1 = 25.00$ | $n_1 = 1.51633$ | $\nu_1 = 64.15$ |
| $r_2 = -7.02$ | | |
| $d_2 = 3.23$ | | |
| $r_3 = -4.615$ | | |
| $d_3 = 16.13$ | $n_2 = 1.64769$ | $\nu_2 = 33.80$ |
| $r_4 = \infty$ | | |
| $d_4 = 1.613$ | $n_3 = 1.72916$ | $\nu_3 = 54.68$ |
| $r_5 = -14.172$ | | |
| $d_5 = 1.613$ | | |
| $r_6 = 14.172$ | | |
| $d_6 = 1.613$ | $n_4 = 1.72916$ | $\nu_4 = 54.68$ |
| $r_7 = \infty$ | | |
| $d_7 = 16.13$ | $n_5 = 1.64769$ | $\nu_5 = 33.80$ |
| $r_8 = 4.615$ | | |
| $d_8 = 3.23$ | | |
| $r_9 = 7.02$ | | |
| $d_9 = 25.00$ | $n_6 = 1.51633$ | $\nu_6 = 64.15$ |
| $r_{10} = -17.698$ | | |
| $f = 41.476$, $\phi_1 = 0.051$, $\phi_2 = -0.140$, $\phi_3 = 0.073$ | | |
| $f(\phi_1 + \phi_2 + \phi_3) = -0.66$ | | |

Embodiment 4 is arranged that the thicknesses $d_3+d_4$ and $d_6+d_7$ of the thick meniscus lenses 22 and 23 are made very large and, at the same time, the airspace $d_2$ between the exit surface $r_2$ of the rod-like biconvex lens 20 and the concave surface $r_3$ of the thick meniscus lens 22 and the airspace $d_8$ between the concave surface $r_8$ of the thick meniscus lens 23 and the entrance surface $r_9$ of the rod-like biconvex lens 21 are made wide. Therefore, the correcting action of the negative surfaces becomes strong and, especially, curvature of field is corrected favourably.

Embodiments 1 through 4 shown in the above are respectively arranged that each of the thick meniscus lenses 22 and 23 is arranged as a cemented doublet consisting of a negative lens element and a positive lens element and that Abbe's number $\nu_n$ of the negative lens element constituting said cemented doublet is smaller than Abbe's number $\nu_p$ of the positive lens element constituting said cemented doublet ($\nu_p > \nu_n$) so as to thereby correct chromatic aberration more favourably.

In said Embodiments 1 through 4, the rod-like biconvex lenses 20 and 21 are very long, and both of the surfaces on the entrance side of the lens 20 and the surface on the exit side of the lens 21 respectively come to positions close to the positions of the transmitted images. Consequently, said surfaces function as field lenses and the other surfaces function as imaging lenses. Therefore, the total focal length of a system composed of the surface on the exit side of the rod-like biconvex lens 20 and the thick meniscus lens 22 has a positive value.

Besides, to prevent the lenses from inclining when they are inserted to an outer tube, the thick meniscus lenses are arranged that the thickness thereof is larger than the diameter thereof.

Figure 3:
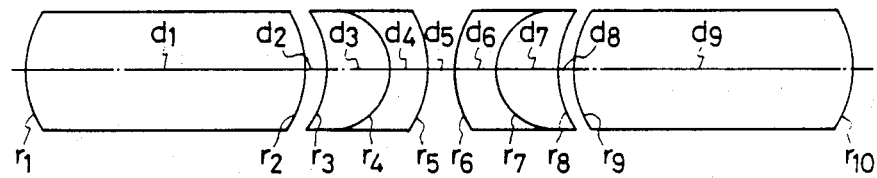
FIG. 3 shows a sectional view of Embodiment 5 of the present invention.

Embodiment 5 of the present invention has the lens configuration shown in FIG. 3, i.e., each of the thick meniscus lenses is arranged as a cemented doublet consisting of a positive lens element and a negative lens element, and has the numerical data shown below.

| | | |
|---|---|---|
| $r_1 = 15.428$ | | |
| $d_1 = 38.92$ | $n_1 = 1.51633$ | $\nu_1 = 64.15$ |
| $r_2 = -14.1379$ | | |

-continued

| | | |
|---|---|---|
| $d_2 = 0.32$ | | |
| $r_3 = -9.056$ | | |
| $d_3 = 1.62$ | $n_2 = 1.51633$ | $\nu_2 = 64.15$ |
| $r_4 = -5.356$ | | |
| $d_4 = 5.48$ | $n_3 = 1.78472$ | $\nu_3 = 25.71$ |
| $r_5 = -10.124$ | | |
| $d_5 = 0.81$ | | |
| $r_6 = 10.124$ | | |
| $d_6 = 5.48$ | $n_4 = 1.78472$ | $\nu_4 = 25.71$ |
| $r_7 = 5.356$ | | |
| $d_7 = 1.62$ | $n_5 = 1.51633$ | $\nu_5 = 64.15$ |
| $r_8 = 9.056$ | | |
| $d_8 = 0.32$ | | |
| $r_9 = 14.1379$ | | |
| $d_9 = 38.92$ | $n_6 = 1.51633$ | $\nu_6 = 64.15$ |
| $r_{10} = -15.428$ | | |
| $f = 40.663$, $\phi_1 = 0.0775$, $\phi_2 = -0.057$ | | |
| $\phi_3 = 0.0365$, $\phi_c = -0.0501$ | | |
| $f(\phi_1 + \phi_2 + \phi_3 + \phi_c) = 0.28$ | | |

In Embodiment 5 shown in the above, the cemented surface in each of the thick meniscus lenses is formed as a surface with strong curvature having negative action and contributes to correction of curvature of field. When each of the thick meniscus lenses has a cemented surface and said cemented surface has refractive power as described in the above, the condition (1) is rewritten as the condition (1') shown below:

$$1 > f(\phi_1 + \phi_2 + \phi_3 + \phi_c) > -1 \qquad (1')$$

where, reference symbol $\phi_c$ represents refractive power of the cemented surface in each of said thick meniscus lenses.

Besides, in Embodiment 5, Abbe's number $\nu_p$ of the positive lens element is made larger than Abbe's number $\nu_n$ of the negative lens element ($\nu_p > \nu_n$) in order to thereby correct chromatic aberration.

Figure 4:
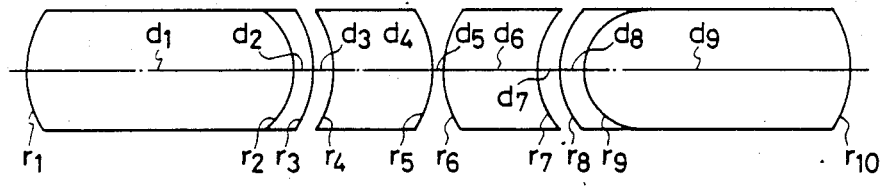
FIG. 4 shows a sectional view of Embodiments 6 and 7 of the present invention.
Figure 5:
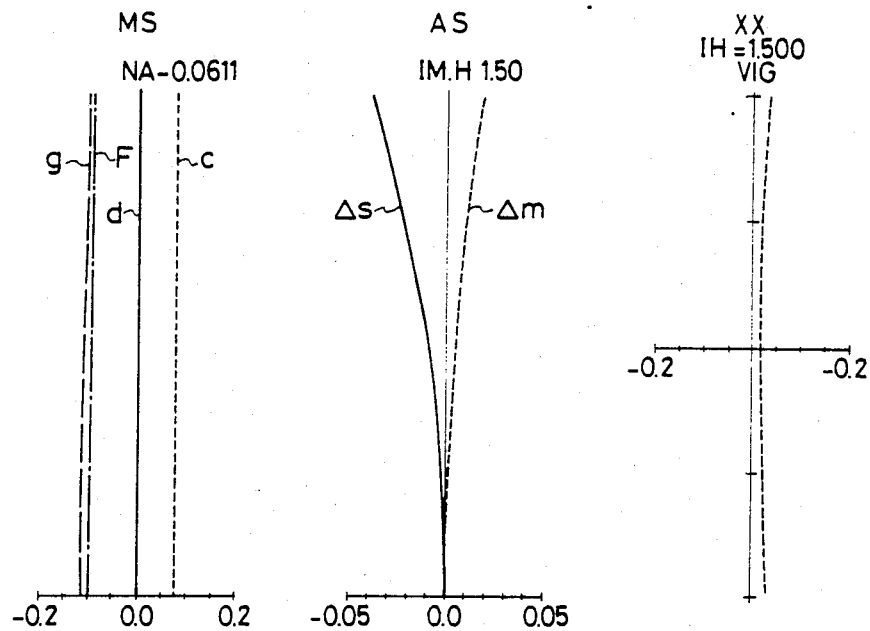
FIGS. 5 through 11 respectively show graphs illustrating aberration curves of Embodiments 1 through 7 of the present invention.
Figure 6:
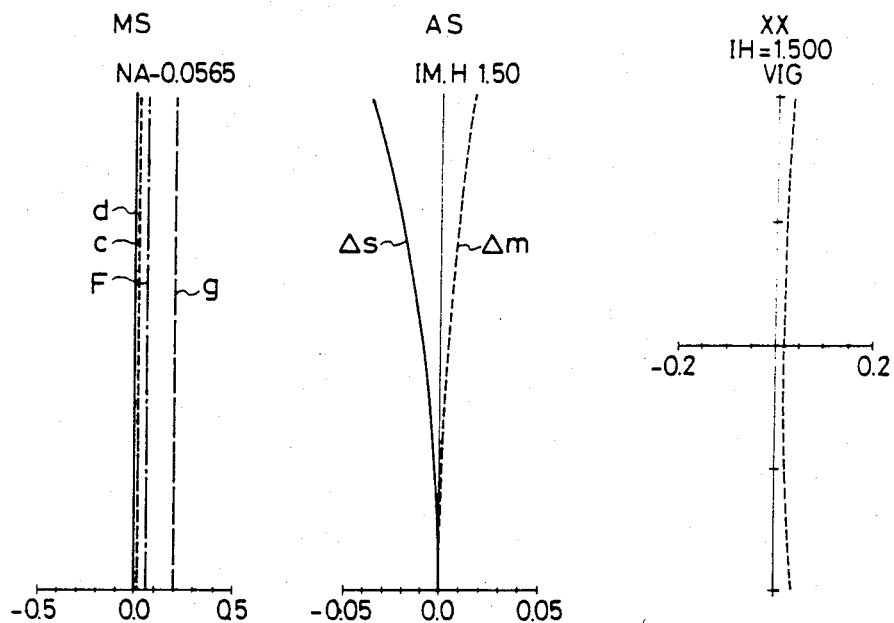
Figure 7:
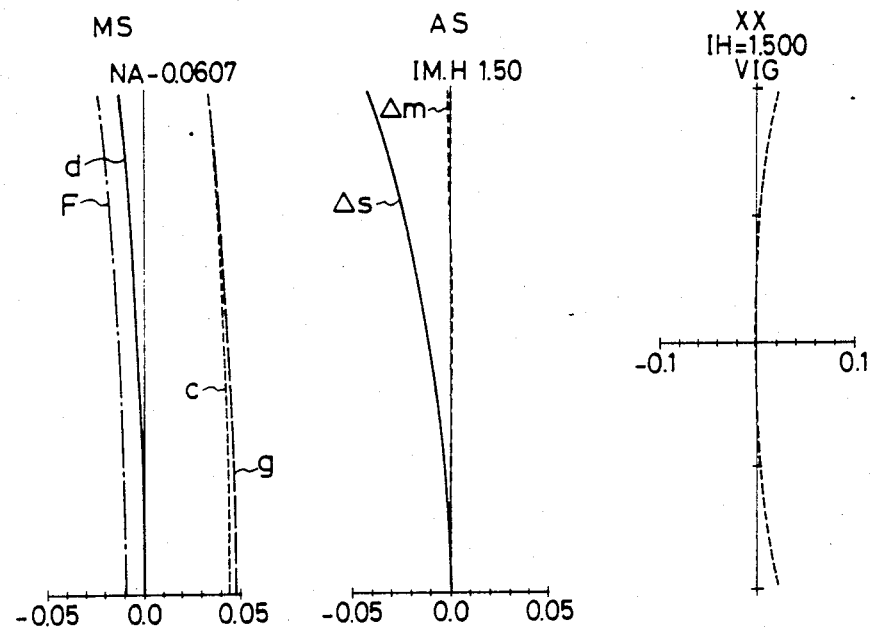
Figure 8:
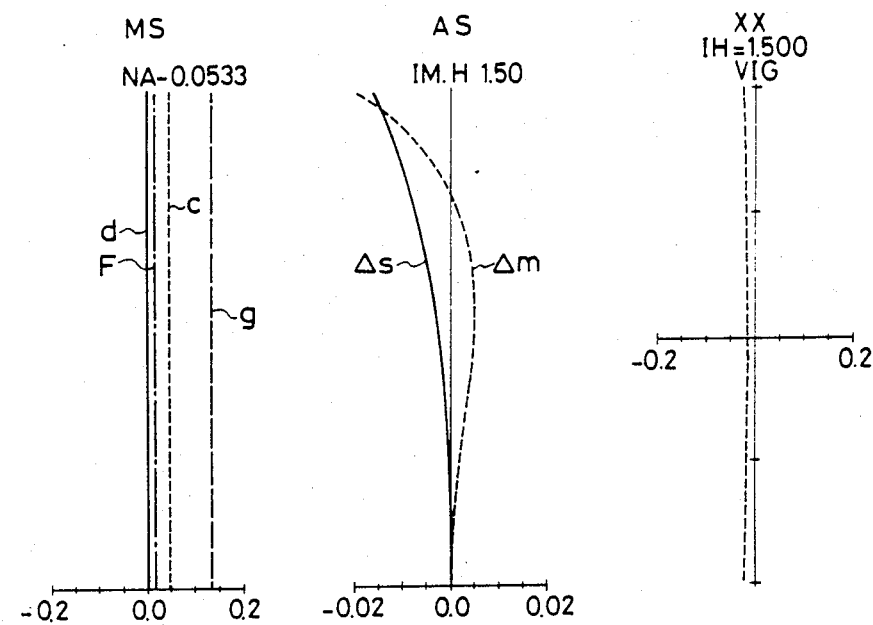
Figure 9:
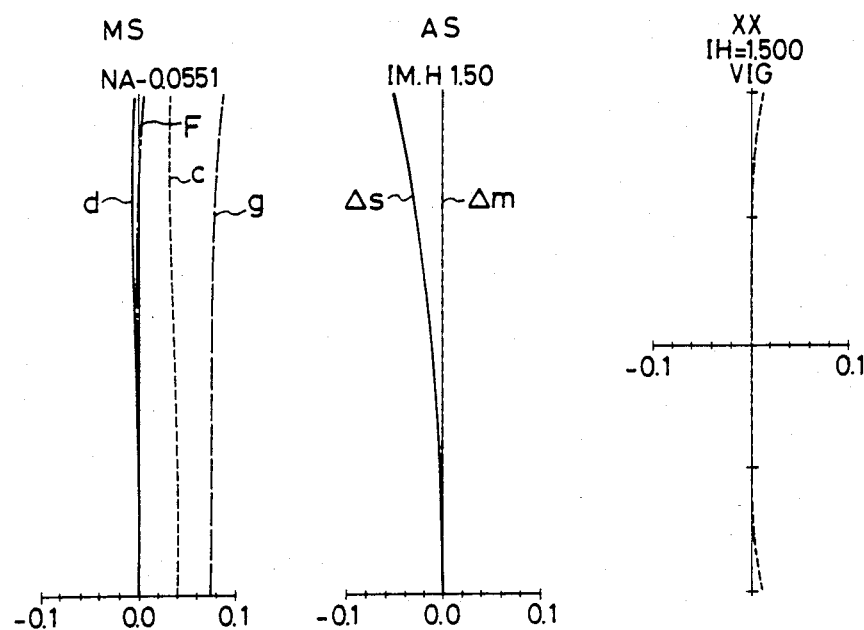
Figure 10:
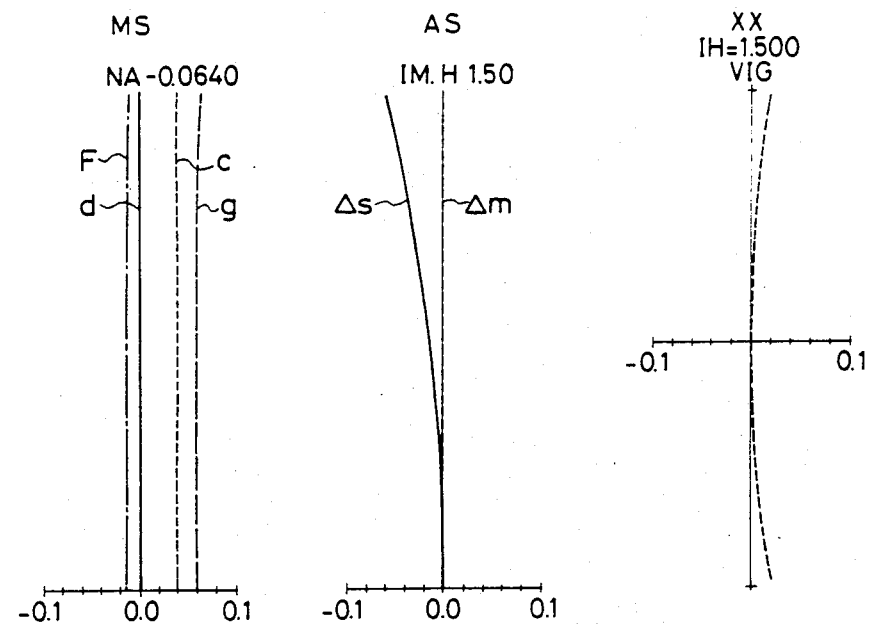
Figure 11:
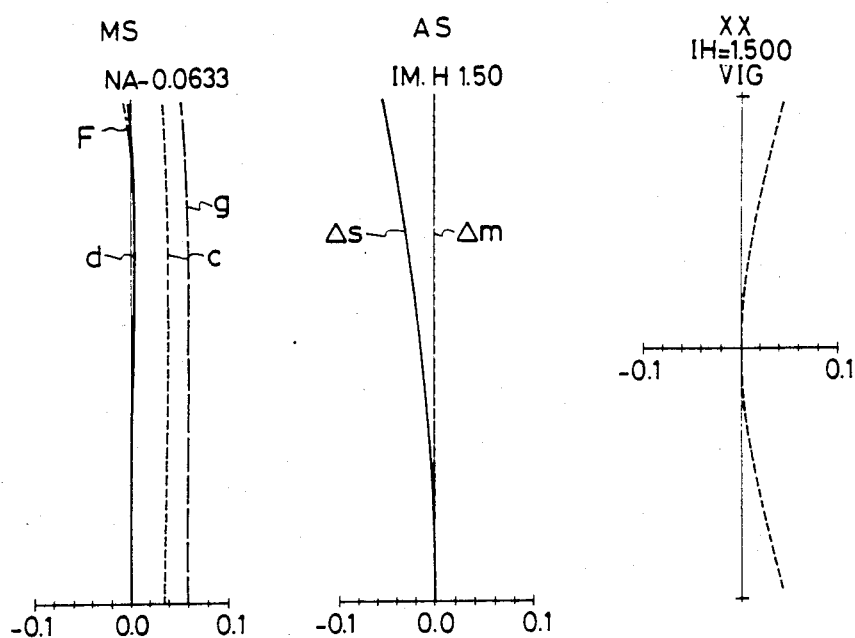

Embodiment 6 of the present invention has the lens configuration shown in FIG. 4, i.e., a negative meniscus lens element is cemented to each of the rod-like biconvex lenses so that said negative meniscus lens element comes to the thick meniscus lens side, and has the numerical data shown below.

| | | |
|---|---|---|
| $r_1 = 18.381$ | | |
| $d_1 = 38.85$ | $n_1 = 1.62$ | $\nu_1 = 36.25$ |
| $r_2 = -5.968$ | | |
| $d_2 = 0.88$ | $n_2 = 1.92286$ | $\nu_2 = 21.29$ |
| $r_3 = -13.477$ | | |
| $d_3 = 2.27$ | | |
| $r_4 = -9.7213$ | | |
| $d_4 = 3.13$ | $n_3 = 1.92286$ | $\nu_3 = 21.29$ |
| $r_5 = -9.926$ | | |
| $d_5 = 3.24$ | | |
| $r_6 = 9.926$ | | |
| $d_6 = 3.13$ | $n_4 = 1.92286$ | $\nu_4 = 21.29$ |
| $r_7 = 9.7213$ | | |
| $d_7 = 2.27$ | | |
| $r_8 = 13.477$ | | |
| $d_8 = 0.88$ | $n_5 = 1.92286$ | $\nu_5 = 21.29$ |
| $r_9 = 5.968$ | | |
| $d_9 = 38.85$ | $n_6 = 1.62$ | $\nu_6 = 36.25$ |
| $r_{10} = -18.381$ | | |
| $f = 35.014$, $\phi_1 = 0.0929$, $\phi_2 = -0.0949$ | | |
| $\phi_3 = 0.0684$, $\phi_c = -0.051$ | | |
| $f(\phi_1 + \phi_2 + \phi_3 + \phi_c) = 0.54$ | | |

Embodiment 7 of the present invention has the lens configuration shown in FIG. 4 in the same way as Embodiment 6 and has the numerical data shown below.

| | | |
|---|---|---|
| $r_1 = 16.848$ | | |
| $d_1 = 39.19$ | $n_1 = 1.51633$ | $\nu_1 = 64.15$ |
| $r_2 = -6.334$ | | |
| $d_2 = 0.62$ | $n_2 = 1.62$ | $\nu_2 = 36.25$ |
| $r_3 = -11.882$ | | |
| $d_3 = 2.43$ | | |
| $r_4 = -5.546$ | | |
| $d_4 = 2.89$ | $n_3 = 1.51633$ | $\nu_3 = 64.15$ |
| $r_5 = -6.705$ | | |
| $d_5 = 3.24$ | | |
| $r_6 = 6.705$ | | |
| $d_6 = 2.89$ | $n_4 = 1.51633$ | $\nu_4 = 64.15$ |
| $r_7 = 5.546$ | | |
| $d_7 = 2.43$ | | |
| $r_8 = 11.882$ | | |
| $d_8 = 0.62$ | $n_5 = 1.62$ | $\nu_5 = 36.25$ |
| $r_9 = 6.334$ | | |
| $d_9 = 39.19$ | $n_6 = 1.51633$ | $\nu_6 = 64.15$ |
| $r_{10} = -16.848$ | | |
| $f = 34.941$, $\phi_1 = 0.077$, $\phi_2 = -0.0931$ | | |
| $\phi_3 = 0.0521$, $\phi_c = -0.0164$ | | |
| $f(\phi_1 + \phi_2 + \phi_3 + \phi_c) = 0.68$ | | |

Figure 13:
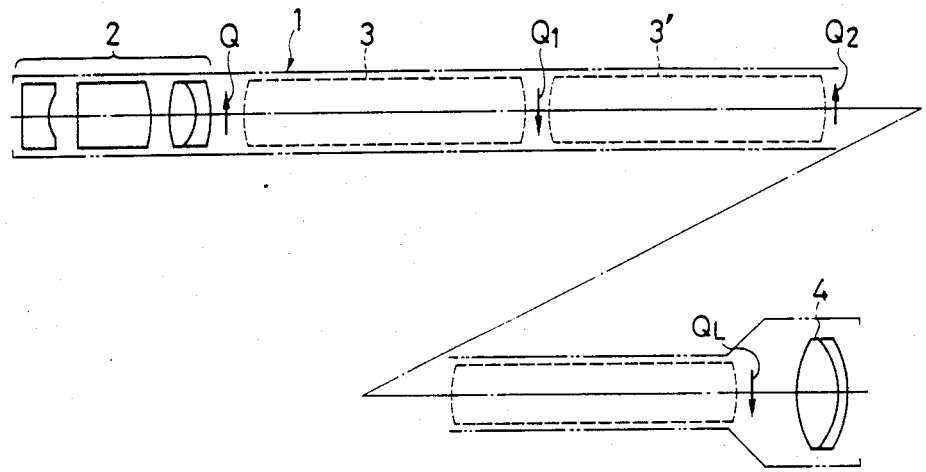
FIG. 13 shows the composition of an optical system of an inflexible-type endoscope.
Figure 14:
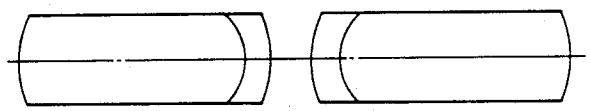
FIGS. 14 and 15 respectively show sectional views of known image transmission optical systems.
Figure 15:
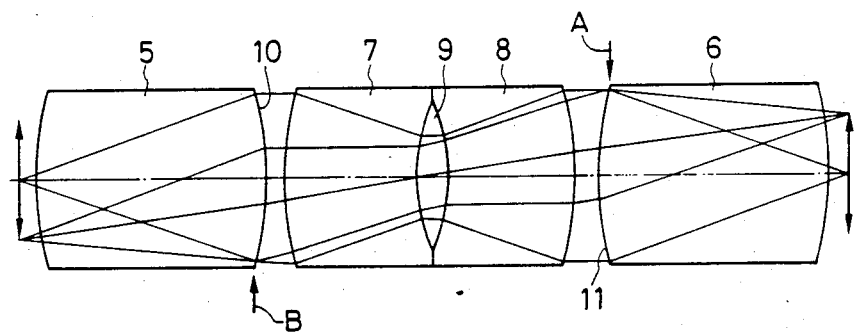

The numerical data of respective embodiments shown in the above are given on the following basis, i.e., the image transmission distance (the distance between $Q_1$ and $Q_2$ in FIG. 13) is regarded as 100 mm.

Graphs of aberration curves of Embodiments 1 through 7 are respectively shown in FIGS. 5 through 11. said graphs of aberration curves are respectively drawn on the following basis, i.e., the diameter of lenses is 4 mm and the diameter of the transmitted image is 3 mm.

Figure 12:
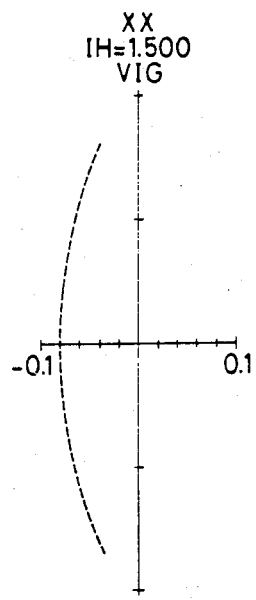
FIG. 12 shows a graph illustrating an aberration curve of coma of a known image transmission optical system.

FIG. 12 shows a graph illustrating an aberration curve of coma which is drawn based on the numerical data of the afore-mentioned known image transmission optical system disclosed in Japanese published unexamined patent application No. 4245/77 and on the same conditions as respective embodiments of the present invention. As it is evident from FIG. 12, in case of said known image transmission optical system, the vignetting factor is 0.83, and rays are considerably limited at the portion of the maximum image height. Therefore, NA is small. On the other hand, in case of embodiments of the present invention, the vignetting factor is larger than 0.95 at the minimum, and this means that the difference between NA at the marginal portion and NA at the central portion is small.

As described so far, by the present invention, it is possible to obtain an image transmission optical system of which curvature of field is corrected favourably and, at the same time, the brightness is uniform from the central portion to the marginal portion.

I claim:

1. An image transmission optical system for an endoscope comprising two rod-like biconvex lenses, and two thick meniscus lenses disposed between said two rod-like biconvex lenses so that the convex surfaces of said two thick meniscus lenses face each other, said biconvex lens disposed on the object side of said two thick meniscus lenses being arranged at a position such that the peripheral rays of the offaxial rays transmitted by said system are limited by said convex surface of the one of said thick meniscus lenses located on the object side, said other of said two rod-like biconvex lenses being disposed on said image side of said two thick meniscus lenses and being disposed at a position such that radially inwardly located offaxial rays transmitted by said system are limited by said convex surface of said two thick meniscus lenses disposed on said image side.

2. An image transmission optical system for an endoscope according to claim 1 in which each of said thick meniscus lenses is arranged as a cemented doublet consisting of a positive lens element and a negative lens element and in which said image transmission optical system for an endoscope fulfills the condition (1') shown below:

$$1 > f(\phi_1 + \phi_2 + \phi_3 + \phi_c) > -1 \quad (1')$$

where, reference symbol $\phi_1$ represents refractive power of the surface on the thick meniscus lens side of each of said rod-like biconvex lenses, reference symbol $\phi_2$ represents refractive power of the concave surface of each of said thick meniscus lenses, reference symbol $\phi_3$ represents refractive power of the convex surface of each of said thick meniscus lenses, reference symbol $\phi_c$ represents refractive power of the cemented surface in each of said thick meniscus lenses, and reference symbol $f$ represents the total focal length of a system composed of said four surfaces.

3. An image transmission optical system for an endoscope according to claim 2 having the following numerical data:

| | | |
|---|---|---|
| $r_1 = 15.428$ | | |
| $d_1 = 38.92$ | $n_1 = 1.51633$ | $\nu_1 = 64.15$ |
| $r_2 = -14.1379$ | | |
| $d_2 = 0.32$ | | |
| $r_3 = -9.056$ | | |
| $d_3 = 1.62$ | $n_2 = 1.51633$ | $\nu_2 = 64.15$ |
| $r_4 = -5.356$ | | |
| $d_4 = 5.48$ | $n_3 = 1.78472$ | $\nu_3 = 25.71$ |
| $r_5 = -10.124$ | | |
| $d_5 = 0.81$ | | |
| $r_6 = 10.124$ | | |
| $d_6 = 5.48$ | $n_4 = 1.78472$ | $\nu_4 = 25.71$ |
| $r_7 = 5.356$ | | |
| $d_7 = 1.62$ | $n_5 = 1.51633$ | $\nu_5 = 64.15$ |
| $r_8 = 9.056$ | | |
| $d_8 = 0.32$ | | |
| $r_9 = 14.1379$ | | |
| $d_9 = 38.92$ | $n_6 = 1.51633$ | $\nu_6 = 64.15$ |
| $r_{10} = -15.428$ | | |
| $f = 40.663$, $\phi_1 = 0.0775$, $\phi_2 = -0.057$ | | |
| $\phi_3 = 0.0365$, $\phi_c = -0.0501$ | | |
| $f(\phi_1 + \phi_2 + \phi_3 + \phi_c) = 0.28$ | | | where, reference symbols $r_1$ through $r_{10}$ respectively represent radii of curvature of respective lens surfaces, reference symbols $d_1$ through $d_9$ respectively represent distances between respective lens surfaces, reference symbols $n_1$ through $n_6$ respectively represent refractive indices of respective lenses, and reference symbols $\nu_1$ through $\nu_6$ respectively represent Abbe's numbers of respective lenses.

4. An image transmission optical system for an endoscope according to claim 1 fulfilling the condition (1) shown below:

$$1 > f(\phi_1 + \phi_2 + \phi_3) > -1 \quad (1)$$

where, reference symbol $\phi_1$ represents refractive power of the surface on the thick meniscus lens side of each of said rod-like biconvex lenses, reference symbol $\phi_2$ represents refractive power of the concave surface of each of said thick meniscus lenses, reference symbol $\phi_3$ represents refractive power of the convex surface of each of said thick meniscus lenses, and reference symbol $f$ represents the total focal length of a system composed of said three surfaces.

5. An image transmission optical system for an endoscope according to claim 4 in which each of said thick meniscus lenses is arranged as a cemented doublet consisting of a plano-concave lens element and a plano-convex lens element and in which said image transmission optical system for an endoscope has the following numerical data:

| | | |
|---|---|---|
| $r_1 = 15.596$ | | |
| $d_1 = 38.89$ | $n_1 = 1.51633$ | $\nu_1 = 64.15$ |
| $r_2 = -14.9578$ | | |
| $d_2 = 0.62$ | | |
| $r_3 = -7.241$ | | |
| $d_3 = 4.49$ | $n_2 = 1.62$ | $\nu_2 = 36.25$ |
| $r_4 = \infty$ | | |
| $d_4 = 2.34$ | $n_3 = 1.734$ | $\nu_3 = 51.49$ |
| $r_5 = -11.637$ | | |
| $d_5 = 0.81$ | | |
| $r_6 = 11.637$ | | |
| $d_6 = 2.34$ | $n_4 = 1.734$ | $\nu_4 = 51.49$ |
| $r_7 = \infty$ | | |
| $d_7 = 4.49$ | $n_5 = 1.62$ | $\nu_5 = 36.25$ |
| $r_8 = 7.241$ | | |
| $d_8 = 0.62$ | | |
| $r_9 = 14.9578$ | | |
| $d_9 = 38.89$ | $n_6 = 1.51633$ | $\nu_6 = 64.15$ |
| $r_{10} = -15.596$ | | |
| $f = 39.625$, $\phi_1 = 0.063$, $\phi_2 = -0.086$ | | |
| $\phi_3 = 0.035$ | | |
| $f(\phi_1 + \phi_2 + \phi_3) = 0.48$ | | | where, reference symbols $r_1$ through $r_{10}$ respectively represent radii of curvature of respective lens surfaces, reference symbols $d_1$ through $d_9$ respectively represent distances between respective lens surfaces, reference symbols $n_1$ through $n_6$ respectively represent refractive indices of respective lenses, and reference symbols $\nu_1$ through $\nu_6$ respectively represent Abbe's numbers of respective lenses.

6. An image transmission optical system for an endoscope according to claim 4 in which each of said thick meniscus lenses is arranged as a cemented doublet consisting of a plano-concave lens element and a plano-convex lens element and in which said image transmission optical system for an endoscope has the following numerical data:

| | | |
|---|---|---|
| $r_1 = 17.544$ | | |
| $d_1 = 33.36$ | $n_1 = 1.51633$ | $\nu_1 = 64.15$ |
| $r_2 = -9.122$ | | |
| $d_2 = 3.03$ | | |
| $r_3 = -5.48$ | | |
| $d_3 = 5.69$ | $n_2 = 1.56732$ | $\nu_2 = 42.83$ |
| $r_4 = \infty$ | | |
| $d_4 = 3.37$ | $n_3 = 1.51633$ | $\nu_3 = 64.15$ |
| $r_5 = -9.121$ | | |
| $d_5 = 2.27$ | | |
| $r_6 = 9.121$ | | |
| $d_6 = 3.37$ | $n_4 = 1.51633$ | $\nu_4 = 64.15$ |
| $r_7 = \infty$ | | |
| $d_7 = 5.69$ | $n_5 = 1.56732$ | $\nu_5 = 42.83$ |
| $r_8 = 5.48$ | | |
| $d_8 = 3.03$ | | |
| $r_9 = 9.122$ | | |
| $d_9 = 33.36$ | $n_6 = 1.51633$ | $\nu_6 = 64.15$ |
| $r_{10} = -17.544$ | | |
| $f = 36.498$, $\phi_1 = 0.057$, $\phi_2 = -0.103$ | | |
| $\phi_3 = 0.057$ | | |
| $f(\phi_1 + \phi_2 + \phi_3) = 0.40$ | | | where, reference symbols $r_1$ through $r_{10}$ respectively represent radii of curvature of respective lens surfaces, reference symbols $d_1$ through $d_9$ respectively represent distances between respective lens surfaces, reference symbols $n_1$ through $n_6$ respectively represent refractive indices of respective lenses, and reference symbols $\nu_1$ through $\nu_6$ respectively represent Abbe's numbers of respective lenses.

7. An image transmission optical system for an endoscope according to claim 4 in which each of said thick meniscus lenses in arranged as a cemented doublet consisting of a plano-concave lens element and a plano-convex lens element and in which said image transmission optical system for an endoscope has the following numerical data:

| | | |
|---|---|---|
| $r_1 = 17.698$ | | |
| $d_1 = 25.00$ | $n_1 = 1.51633$ | $\nu_1 = 64.15$ |
| $r_2 = -7.02$ | | |
| $d_2 = 3.23$ | | |
| $r_3 = -4.615$ | | |
| $d_3 = 16.13$ | $n_2 = 1.64769$ | $\nu_2 = 33.80$ |
| $r_4 = \infty$ | | |
| $d_4 = 1.613$ | $n_3 = 1.72916$ | $\nu_3 = 54.68$ |
| $r_5 = -14.172$ | | |
| $d_5 = 1.613$ | | |
| $r_6 = 14.172$ | | |
| $d_6 = 1.613$ | $n_4 = 1.72916$ | $\nu_4 = 54.68$ |
| $r_7 = \infty$ | | |
| $d_7 = 16.13$ | $n_5 = 1.64769$ | $\nu_5 = 33.80$ |
| $r_8 = 4.615$ | | |
| $d_8 = 3.23$ | | |
| $r_9 = 7.02$ | | |
| $d_9 = 25.00$ | $n_6 = 1.51633$ | $\nu_6 = 64.15$ |
| $r_{10} = -17.698$ | | |
| $f = 41.476$, $\phi_1 = 0.051$, $\phi_2 = -0.140$ | | |
| $\phi_3 = 0.073$ | | |
| $f(\phi_1 + \phi_2 + \phi_3) = -0.66$ | | | where, reference symbols $r_1$ through $r_{10}$ respectively represent radii of curvature of respective lens surfaces, reference symbols $d_1$ through $d_9$ respectively represent distances between respective lens surfaces, reference symbols $n_1$ through $n_6$ respectively represent refractive indices of respective lenses, and reference symbols $\nu_1$ through $\nu_6$ respectively represent Abbe's numbers of respective lenses.

8. An image transmission optical system for an endoscope according to claim 1 further comprising two negative meniscus lens elements respectively cemented to said rod-like biconvex lenses and fulfilling the condition (1') shown below:

$$(1') \quad 1 > f(\phi_1 + \phi_2 + \phi_3 + \phi_c) > -1 \tag{1'}$$

where, reference symbol $\phi_1$ represents refractive power of the surface on the thick meniscus lens side of each of said rod-like biconvex lenses, reference symbol $\phi_2$ represents refractive power of the concave surface of each of said thick meniscus lenses, reference symbol $\phi_3$ represents refractive power of the convex surface of each of said thick meniscus lenses, reference symbol $\phi_c$ represents refractive power of the cemented surface between each of said rod-like biconvex lenses and each of said negative meniscus lens elements, and reference symbol f represents the total focal length of a system composed of said four surfaces.

9. An image transmission optical system for an endoscope according to claim 8 having the following numerical data:

| | | |
|---|---|---|
| $r_1 = 18.381$ | | |
| $d_1 = 38.85$ | $n_1 = 1.62$ | $\nu_1 = 36.25$ |
| $r_2 = -5.968$ | | |
| $d_2 = 0.88$ | $n_2 = 1.92286$ | $\nu_2 = 21.29$ |

-continued

| | | |
|---|---|---|
| $r_3 = -13.477$ | | |
| $d_3 = 2.27$ | | |
| $r_4 = -9.7213$ | | |
| $d_4 = 3.13$ | $n_3 = 1.92286$ | $\nu_3 = 21.29$ |
| $r_5 = -9.926$ | | |
| $d_5 = 3.24$ | | |
| $r_6 = 9.926$ | | |
| $d_6 = 3.13$ | $n_4 = 1.92286$ | $\nu_4 = 21.29$ |
| $r_7 = 9.7213$ | | |
| $d_7 = 2.27$ | | |
| $r_8 = 13.477$ | | |
| $d_8 = 0.88$ | $n_5 = 1.92286$ | $\nu_5 = 21.29$ |
| $r_9 = 5.968$ | | |
| $d_9 = 38.85$ | $n_6 = 1.62$ | $\nu_6 = 36.25$ |
| $r_{10} = -18.381$ | | |

$$f = 35.014, \phi_1 = 0.0929, \phi_2 = -0.0949$$
$$\phi_3 = 0.0684, \phi_c = -0.051$$
$$f(\phi_1 + \phi_2 + \phi_3 + \phi_c) = 0.54$$

where, reference symbols $r_1$ through $r_{10}$ respectively represent radii of curvature of respective lens surfaces, reference symbols $d_1$ through $d_9$ respectively represent distances between respective lens surfaces, reference symbols $n_1$ through $n_6$ respectively represent refractive indices of respective lenses, and reference symbols $\nu_1$ through $\nu_6$ respectively represent Abbe's numbers of respective lenses.

10. An image transmission optical system for an endoscope according to claim 8 having the following numerical data:

| | | |
|---|---|---|
| $r_1 = 16.848$ | | |
| $d_1 = 39.19$ | $n_1 = 1.51633$ | $\nu_1 = 64.15$ |
| $r_2 = -6.334$ | | |
| $d_2 = 0.62$ | $n_2 = 1.62$ | $\nu_2 = 36.25$ |
| $r_3 = -11.882$ | | |
| $d_3 = 2.43$ | | |
| $r_4 = -5.546$ | | |
| $d_4 = 2.89$ | $n_3 = 1.51633$ | $\nu_3 = 64.15$ |
| $r_5 = -6.705$ | | |
| $d_5 = 3.24$ | | |
| $r_6 = 6.705$ | | |
| $d_6 = 2.89$ | $n_4 = 1.51633$ | $\nu_4 = 64.15$ |
| $r_7 = 5.546$ | | |
| $d_7 = 2.43$ | | |
| $r_8 = 11.882$ | | |
| $d_8 = 0.62$ | $n_5 = 1.62$ | $\nu_5 = 36.25$ |
| $r_9 = 6.334$ | | |
| $d_9 = 39.19$ | $n_6 = 1.51633$ | $\nu_6 = 64.15$ |
| $r_{10} = -16.848$ | | |

$$f = 34.941, \phi_1 = 0.077, \phi_2 = -0.0931$$
$$\phi_3 = 0.0521, \phi_c = -0.0164$$
$$f(\phi_1 + \phi_2 + \phi_3 + \phi_c) = 0.68$$

where, reference symbols $r_1$ through $r_{10}$ respectively represent radii of curvature of respective lens surfaces, reference symbols $d_1$ through $d_9$ respectively represent distances between respective lens surfaces, reference symbols $n_1$ through $n_6$ respectively represent refractive indices of respective lenses, and reference symbols $\nu_1$ through $\nu_6$ respectively represent Abbe's numbers of respective lenses.

11. An image transmission optical system for an endoscope comprising two rod-like biconvex lenses, and two thick meniscus lenses arranged between said two rod-like biconvex lenses so that the convex surfaces of said two thick meniscus lenses face each other, said lenses fulfilling the condition (1) shown below:

$$1 > f(\phi_1 + \phi_2 + \phi_3) > -1 \quad (1)$$

where, reference symbol, $\phi_1$ represents refractive power of the surface of the thick meniscus lens side of each of said rod-like biconvex lenses, reference symbol $\phi_2$ represents refractive power of the concave surface of each of said thick meniscus lenses, reference symbol $\phi_3$ represents refractive power of the convex surface of each of said thick meniscus lenses, and reference symbol f represents the total focal length of a system composed of said three surfaces;

each of said thick meniscus lenses being arranged as a cemented doublet consisting of a plano-concave lens element and a plano-convex lens element and in which said image transmission optical system for an endoscope has the following numerical data:

| | | |
|---|---|---|
| $r_1 = 17.792$ | | |
| $d_1 = 38.89$ | $n_1 = 1.62$ | $\nu_1 = 36.25$ |
| $r_2 = -16.305$ | | |
| $d_2 = 0.62$ | | |
| $r_3 = -7.583$ | | |
| $d_3 = 4.49$ | $n_2 = 1.62$ | $\nu_2 = 36.25$ |
| $r_4 = \infty$ | | |
| $d_4 = 2.34$ | $n_3 = 1.6968$ | $\nu_3 = 55.52$ |
| $r_5 = -11.618$ | | |
| $d_5 = 1.00$ | | |
| $r_6 = 11.618$ | | |
| $d_6 = 2.34$ | $n_4 = 1.6968$ | $\nu_4 = 55.52$ |
| $r_7 = \infty$ | | |
| $d_7 = 4.49$ | $n_5 = 1.62$ | $\nu_5 = 36.25$ |
| $r_8 = 7.583$ | | |
| $d_8 = 0.62$ | | |
| $r_9 = 16.305$ | | |
| $d_9 = 38.89$ | $n_6 = 1.62$ | $\nu_6 = 36.25$ |
| $r_{10} = -17.792$ | | |

$$f = 36.82, \phi_1 = 0.06, \phi_2 = -0.082, \phi_3 = 0.038$$
$$f(\phi_1 + \phi_2 + \phi_3) = 0.59$$

where, reference symbols $r_1$ through $r_{10}$ respectively represent radii of curvature of respective lens surfaces, reference symbols $d_1$ through $d_9$ respectively represent distances between respective lens surfaces, reference symbols $n_1$ through $n_6$ respectively represent refractive indices of respective lenses, and reference symbols $\nu_1$ through $\nu_6$ respectively represent Abbe's numbers of respective lenses.

* * * * *